(12) United States Patent
Nakakado (10) Patent No.: US 8,257,527 B2
(45) Date of Patent: Sep. 4, 2012

(54) LAMINATED STRETCHABLE SHEET AND METHOD FOR PRODUCING THE SAME

(75) Inventor: Masaki Nakakado, Osaka (JP)

(73) Assignee: Zuiko Corporation, Osaka (JP)

( * ) Notice: Subject to any disclaimer, the term of this patent is extended or adjusted under 35 U.S.C. 154(b) by 532 days.

(21) Appl. No.: 12/527,444

(22) PCT Filed: Mar. 31, 2008

(86) PCT No.: PCT/JP2008/056292
§ 371 (c)(1),
(2), (4) Date: Aug. 17, 2009

(87) PCT Pub. No.: WO2008/126709
PCT Pub. Date: Oct. 23, 2008

(65) Prior Publication Data
US 2010/0112313 A1 May 6, 2010

(30) Foreign Application Priority Data
Apr. 10, 2007 (JP) .................. 2007-102474

(51) Int. Cl.
*B32B 37/00* (2006.01)
(52) U.S. Cl. ........ 156/73.1; 156/164; 156/229; 156/290
(58) Field of Classification Search ............. 156/73.1, 156/160, 163, 164, 229, 290, 308.2, 308.4
See application file for complete search history.

(56) References Cited

U.S. PATENT DOCUMENTS
5,576,090 A 11/1996 Suzuki
6,059,764 A * 5/2000 Osborn et al. ........... 604/385.22
7,833,211 B2 * 11/2010 Mansfield ............... 604/385.22
(Continued)

FOREIGN PATENT DOCUMENTS
JP 5-228177 9/1993
(Continued)

OTHER PUBLICATIONS
International Search Report for corresponding Application No. PCT/JP2008/056292 dated Jul. 1, 2008.

*Primary Examiner* — James Sells
(74) *Attorney, Agent, or Firm* — Renner, Otto, Boisselle & Sklar, LLP (57) ABSTRACT

A laminated stretchable sheet and a method for producing the same of the present invention include: a step of shrinking the continuous sheets W1 and W2 in a width direction Y along folding lines WL extending in the flow direction of continuous sheets W1 and W2 thereby forming slack portions W1b and W2b that can be stretched; a step of placing an elastic member F that can be stretched in the width direction Y on the continuous sheets W1 and W2 while the elastic member F is aligned with the slack portions W1b and W2b; a step of attaching at least opposite end portions of the elastic member F in the width direction Y to the continuous sheets W1 and W2, during the placement, thereby forming a composite sheet; a step of stretching the slack portions W1b and W2b and the elastic member F in the width direction Y; and a step of attaching together the continuous sheets W1 and W2 and the elastic member F intermittently in an intermediate portion between the opposite end portions.

4 Claims, 13 Drawing Sheets

U.S. PATENT DOCUMENTS 8,211,256 B2 * 7/2012 Nakakado .................... 156/73.1

FOREIGN PATENT DOCUMENTS

| | | |
|---|---|---|
| JP | 2003-508095 | 3/2003 |
| JP | 2004-223238 | 8/2004 |
| JP | 3670289 | 4/2005 |
| JP | 2006-212307 | 8/2006 |
| JP | 2006-230839 | 9/2006 |
| WO | 96/24319 | 8/1996 |
| WO | 00/37005 | 6/2000 |

* cited by examiner

LAMINATED STRETCHABLE SHEET AND METHOD FOR PRODUCING THE SAME

TECHNICAL FIELD

The present invention relates to a laminated stretchable sheet, and a method for producing the same.

BACKGROUND ART

In the prior art, there are cases where a laminated stretchable sheet including two non-woven fabrics and a thermoplastic elastic sheet placed therebetween is used as a composite sheet for use in a disposable diaper, or the like, particularly, as a composite sheet for use in a waist portion of a pants-type diaper, or the like, in order to improve the fit of the diaper (see the first, second and third patent documents).

[First Patent Document] Japanese Patent No. 3670289 (page 4, right column)

[Second Patent Document] Japanese Laid-Open Patent Publication No. 2006-230839 (Paragraph [0021])

[Third Patent Document] Japanese Laid-Open Patent Publication No. 2004-223238 (Paragraph [0021])

DISCLOSURE OF THE INVENTION

Japanese Patent No. 3670289 discloses a method for producing a side panel by attaching an elastic member to a non-woven fabric by applying an adhesive on the non-woven fabric in a spiral pattern (spiral coating).

Japanese Laid-Open Patent Publication No. 2006-230839 discloses attaching an elastic member to a non-woven fabric by applying an adhesive, which is a hotmelt resin, on the elastic member.

Japanese Laid-Open Patent Publication No. 2004-223238 discloses attaching an elastic member and a non-woven fabric to each other by applying an adhesive on the elastic member or the web.

With the inventions of these documents, however, an adhesive is applied entirely across the bonding surface of the elastic member, and the adhesive therefore deteriorates the feel of the side panel by, for example, introducing stiffness thereto. Moreover, since a hotmelt adhesive is expensive, it will lead to a high material cost.

It is therefore a primary object of the present invention to provide a laminated stretchable sheet which gives a desirable wearability and with which the production cost can be reduced, and a method for producing the same.

A method for producing a laminated stretchable sheet of the present invention includes: a step of slackening a continuous sheet, which is continuous, in a width direction perpendicular to a flow direction of the continuous sheet, thereby forming a slack portion that can be elongated in the continuous sheet; a step of placing an elastic member that can be stretched in the width direction of the continuous sheet on the continuous sheet so that the elastic member bridges over the slack portion; a step of attaching at least opposite end portions of the elastic member in the width direction to the continuous sheet, during the placement, thereby forming a composite sheet; a step of stretching the slack portion and the elastic member in the width direction; and a step of attaching together the continuous sheet and the elastic member intermittently in an intermediate portion between the opposite end portions, while being in the stretched state.

With this method, since an adhesive is applied only in the opposite end portions of the elastic member, and no adhesive is applied in portions other than the opposite end portions of the elastic member, stiffness, etc., due to the adhesive, is suppressed, and the feel is less likely to deteriorate. Moreover, since it is possible to reduce the amount of the expensive adhesive as much as possible, it is possible to achieve a significant cost reduction.

Furthermore, if an inexpensive thread-like elastic member is used as the elastic member, it is possible to achieve a further cost reduction. The thread-like elastic member may be, for example, an elastic thread, such as a rubber thread.

If a thread-like elastic member is employed, the thread-like elastic member is sandwiched between two continuous sheets.

That is, another method for producing a laminated stretchable sheet of the present invention includes: a step of slackening two continuous sheets, which are continuous, in a width direction perpendicular to a flow direction of the continuous sheets, thereby forming slack portions that can be elongated in the continuous sheets; a step of carrying the two continuous sheets with the slack portions of these continuous sheets facing each other; a step of placing an elastic member that can be stretched in the width direction of the continuous sheets between the two continuous sheets so as to bridge over the slack portions and so as to be sandwiched between the two continuous sheets; a step of attaching at least opposite end portions of the elastic member in the width direction to the continuous sheets, during the placement, thereby forming a composite sheet; a step of stretching these slack portions and the elastic member in the width direction; and a step of attaching together the two continuous sheets intermittently in an intermediate portion between the opposite end portions, while being in the stretched state.

In such a case, it is preferred that only the two continuous sheets are ultrasonically attached to each other in the intermediate portion, without attaching the thread-like elastic member thereto.

This is for preventing the elasticity (stretchability) of the elastic member from being deteriorated by the ultrasonic attachment.

On the other hand, a laminated stretchable sheet of the present invention is a laminated stretchable sheet, including at least two non-woven fabrics containing thermoplastic fibers therein, and a thread-like elastic member sandwiched between the two non-woven fabrics, the laminated stretchable sheet having a stretching portion that can be stretched in a predetermined stretch direction, wherein the elastic member is placed in a wave-shaped pattern having an amplitude in the stretch direction and can be stretched in the stretch direction; the elastic member is attached to the two non-woven fabrics via an adhesive in bonding portions at or near opposite vertexes of the amplitude of the wave shape; and no adhesive is interposed between the two non-woven fabrics in an intermediate portion between the two bonding portions at opposite ends, and the two non-woven fabrics are welded to each other in the intermediate portion.

In the present laminated stretchable sheet, no adhesive is used, and the two non-woven fabrics are welded to each other, in a portion between bonding portions where the non-woven fabrics are bonded together by an adhesive, i.e., in the intermediate portion. Therefore, it is possible to improve the feel and achieve a cost reduction.

Particularly, since a thread-like elastic member is placed in a wave shape, it can be used in a portion different from those in which many elastic threads parallel to each other are placed, e.g., a side panel, or the like.

In the present laminated stretchable sheet, it is preferred that the two non-woven fabrics are welded to each other intermittently at a plurality of positions in the intermediate portion.

In such a case, since welding is not done across the entire surface, the feel is further improved.

DESCRIPTION OF THE REFERENCE NUMERALS

A1, A2: Opposite end portion
F, F1: Elastic member (elastic sheet)
W1: First continuous sheet (first non-woven fabric)
W1a, W2a: Central portion
W1b, W2b: Slack portion
W2: Second continuous sheet (second non-woven fabric)
W3: Composite sheet
Wm: Intermediate portion
WL: Folding line
Y: Width direction
X: Carrying direction

BEST MODE FOR CARRYING OUT THE INVENTION

Embodiment 1

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

Embodiments of the present invention will now be described with reference to the drawings.

While the present laminated stretchable sheet can be used in various applications, the following description will be directed to a case where the present laminated stretchable sheet is applied to a side panel of a diaper.

Diaper 3:

FIGS. 1A to 4C show Embodiment 1.

Figure 4A:
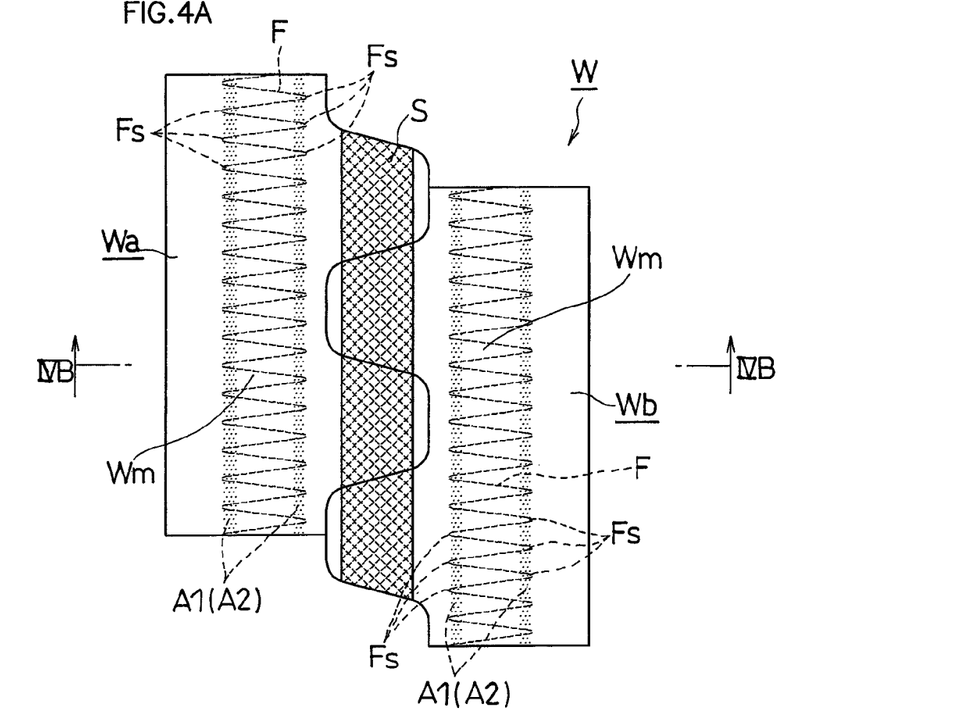
FIG. 4A is a schematic plan view showing an example of a laminated stretchable sheet.
Figure 4B:
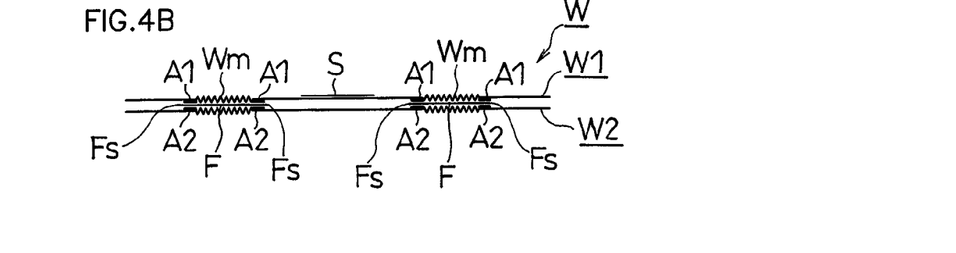
FIG. 4B is a schematic cross-sectional view thereof.
Figure 4C:
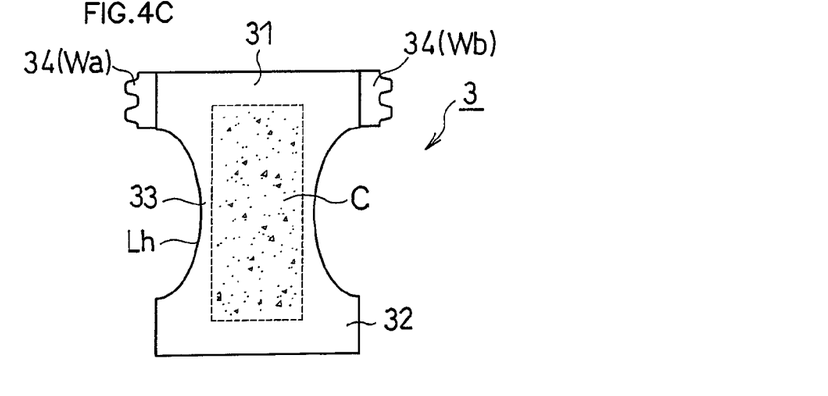
FIG. 4C is a schematic plan view showing a diaper.

As shown in FIG. 4C, a diaper 3 includes, formed as an integral piece, torso portions 31 and 32 covering the torso of the wearer and a crotch portion 33 covering the crotch of the wearer. The crotch portion 33 includes a core portion C including an absorbent body. In the crotch portion 33, leg holes Lh are formed for fitting the edge portion of the crotch portion 33 around the legs of the wearer.

The torso portions 31 and 32 include the rear torso portion 31 covering a back portion of the wearer, and the front torso portion 32 covering an abdominal portion of the wearer. The core portion C is placed between the rear torso portion 31 and the front torso portion 32. Flaps 34 formed by a laminated stretchable sheet W (FIG. 4B) are attached to opposite sides of the rear torso portion 31.

Laminated Stretchable Sheet W:

As shown in FIG. 4B, the laminated stretchable sheet W includes a thread-like elastic member (e.g., a rubber thread) F sandwiched between two non-woven fabrics W1 and W2 containing thermoplastic fibers therein.

As shown in FIG. 4A, the elastic member F is placed in a wave-shaped pattern having an amplitude in a stretch direction thereof and is placed so as to be stretchable in the stretch direction. As shown in FIG. 4B, the elastic member F is attached to the two non-woven fabrics W1 and W2 via an adhesive in bonding portions A1 and A2 at opposite vertexes Fs and Fs of the amplitude of the wave shape.

No pressure-sensitive adhesive or adhesive is interposed between the two non-woven fabrics W1 and W2 in an intermediate portion Wm between the bonding portions A1 and A2 shown in FIG. 4A. On the other hand, in the intermediate portion Wm, the two non-woven fabrics W1 and W2 are intermittently welded to each other. Ultrasonic attachment, for example, may be used as the method for the welding. It is preferred that the ultrasonic attachment is done at a plurality of positions in the intermediate portion Wm while avoiding the elastic member F.

Production Method:

Non-Woven Fabrics W1 and W2

Figures 1A, 1B:
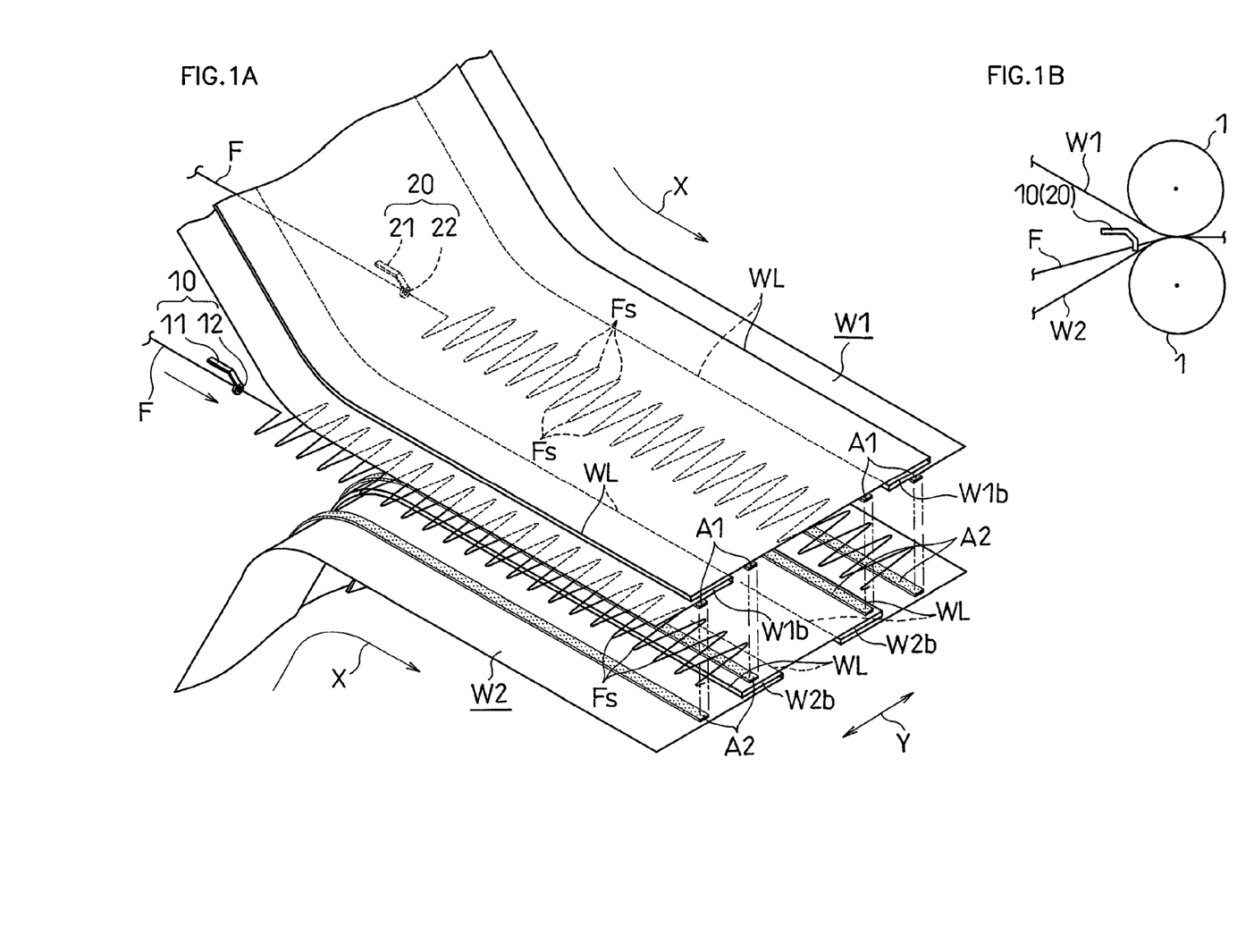
FIG. 1A is a schematic perspective view showing a part of a production step for producing a laminated stretchable sheet according to Embodiment 1 of the present invention.
FIG. 1B is a schematic side view showing a part of an example of a production apparatus for producing the laminated stretchable sheet.
Figure 2A:
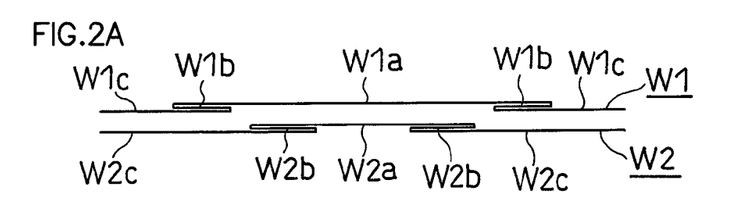
FIGS. 2A, 2B, 2C and 2D are schematic cross-sectional views showing a method for producing a laminated stretchable sheet.

First, as shown in FIG. 1A, the first and second continuous sheets W1 and W2 are bent, and slackened, along folding lines WL (FIG. 1A) into a generally Z-shape pattern or a generally Q-shape pattern, and then they are further folded up, thereby forming slack portions W1b and W2b. As shown in FIG. 1A, the folding lines WL extend along the carrying direction X of the continuous sheets W1 and W2. The slack portions W1b and W2b shown in FIG. 2A are formed between the opposite end portions W1c and W1c (W2c and W2c) of the two continuous sheets W1 and W2, respectively. Central portions W1a (W2a) are formed between the slack portions W1b and W1b (W2b and W2b), respectively.

Figure 2B:
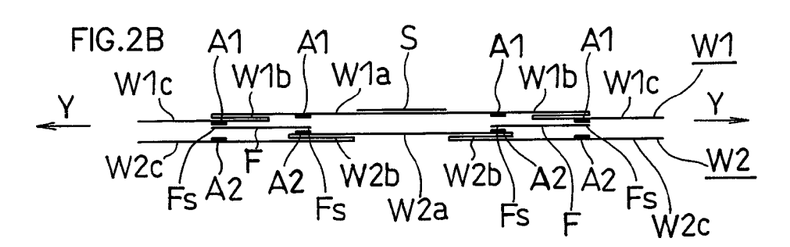
Figure 2C:
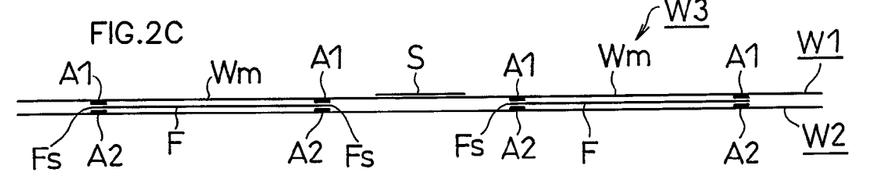
Figure 2D:
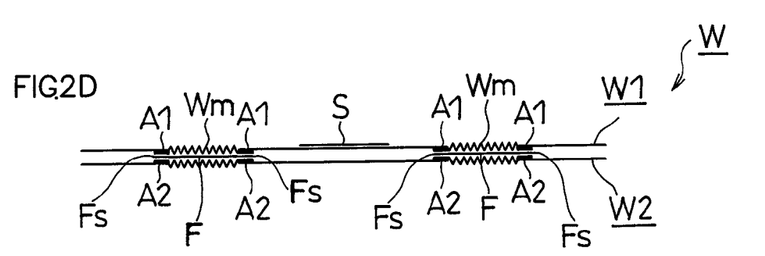
Figure 3:
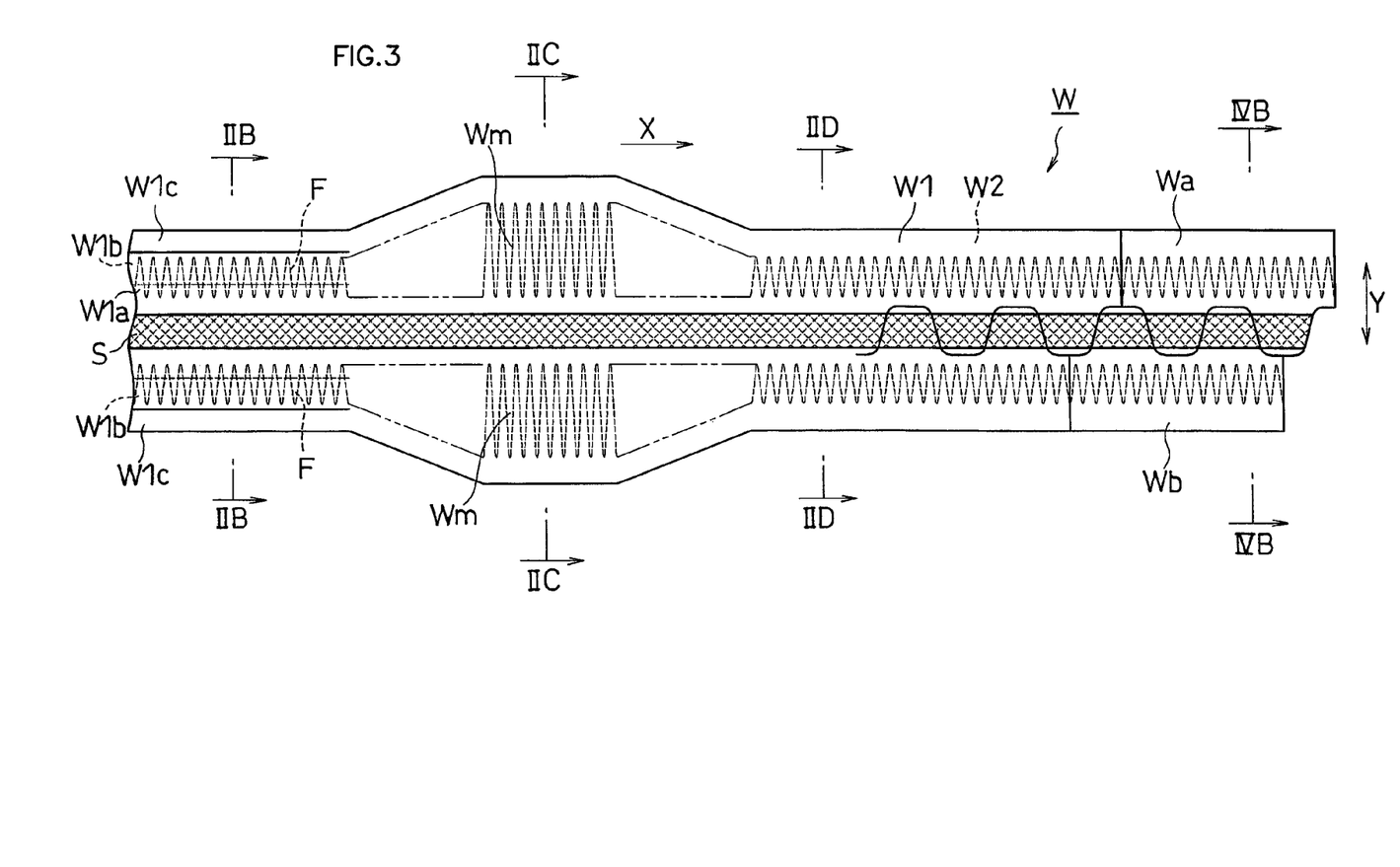
FIG. 3 is a schematic plan view showing a method for producing a laminated stretchable sheet.

The slack portions W1b and W1b of the first continuous sheet W1 and the slack portions W2b and W2b of the second continuous sheet W2 are formed at such positions that they face each other in a state where it is used as shown in FIGS. 2C and 2D (in a state where the continuous sheets W1 and W2 are pulled outwardly in the width direction Y (FIG. 2)).

After the formation of the slack portions, the elastic members F and F, which are stretchable in the width direction Y generally perpendicular to the carrying direction X of the continuous sheets W1 and W2, are placed between the continuous sheets W1 and W2, as shown in FIGS. 1A and 2B, thus producing the laminated stretchable sheet W. The elastic member F is placed between the slack portions W1b and W2b formed near one end portion of the continuous sheets W1 and W2, and between the slack portions W1b and W2b formed near the other end portion thereof.

In this embodiment, the elastic member F is an elastic thread, and is supplied so as to be sandwiched between the continuous sheets W1 and W2 by nip rolls 1 and 1 as shown in FIG. 1B.

As shown in FIG. 1A, the elastic members F are guided between the continuous sheets W1 and W2 by first and second guides 10 and 20. The guides 10 and 20 reciprocate in the width direction Y, and include first and second arms 11 and 21, respectively. First and second guide portions 12 and 22, each having one or more elastic member passing holes, are provided at the tip portion of the arms 11 and 21, respectively. At least one thread of the elastic member F is passed through each elastic member passing hole. As the arms 11 and 21 move, the elastic members F passing through the elastic member passing holes of the arms 11 and 21 are dispensed in a wave-shaped pattern between the continuous sheets W1 and W2.

Note that the method of Japanese Laid-Open Patent Publication No. 2003-111796 may be employed as the method for supplying the elastic member F.

An adhesive is applied in advance on predetermined portions A1 and A2 of the continuous sheets W1 and W2 shown in FIGS. 1A and 2B. As a result, only portions of the elastic members F that are near the opposite end portions Fs in the width direction Y are attached to the continuous sheets W1 and W2 by the adhesive.

Together with the placement of the elastic members. F, a touch fastener S shown in FIG. 4A is attached to a central portion of the surface of one continuous sheet W1.

Then, as left and right end portions W1c and W2c of the continuous sheets W1 and W2 shown in FIG. 2B are drawn in the width direction Y, the folded (slackened) slack portions W1b and W2b are drawn outwardly in the width direction Y, while the elastic members F are stretched, as shown in FIG. 2C, thus producing the composite sheet W3. After the stretching, the ultrasonic attachment is done in the intermediate portion Wm shown in FIG. 3, thereby welding together the continuous sheets W1 and W2 intermittently (e.g., in a scattered pattern) at a plurality of positions. Note that it is preferred that the ultrasonic attachment is done only at positions avoiding the elastic members F.

After the ultrasonic attachment, the stretching of the intermediate portion Wm and the elastic members F is released so that they are allowed to return to the free length, as shown in FIG. 2D, thus producing the laminated stretchable sheet W.

Then, as shown in FIG. 4A, the central portion of the laminated stretchable sheet W is slit in a predetermined wave-shaped pattern along the carrying direction X, and the laminated stretchable sheet W is cut off along the width direction Y into pieces of a predetermined length, thus producing cut-off sheets Wa and Wb to be the flaps 34 (FIG. 4C).

It is preferred that after the slitting, the phases of the continuous cut-off sheets are aligned with each other by, for example, relatively lowering the carrying speed of one continuous cut-off sheet from that of the other continuous cut-off sheet. After the cutting off, the phases of the two cut-off sheets Wa and Wb may be aligned with each other by, for example, relatively lowering the carrying speed of one cut-off sheet Wa (Wb) from that of the other cut-off sheet Wb (Wa). Then, the cut-off sheets Wa and Wb may be attached to the opposite end portions of the rear torso portion 31 of the diaper 3 shown in FIG. 4C, thus forming the diaper 3.

Note that the continuous sheets W1 and W2 may be slit and separated into two in advance, and the elastic members F may be placed thereon after the slitting or after the separation.

Embodiment 2

FIGS. 5 to 8C Show Embodiment 2.
Diaper 3A:
In Embodiment 2, a sheet-like elastic member F1 made of a thermoplastic resin is used, instead of the rubber thread. The sheet-like elastic member F1 shown in FIG. 8A is employed for the flaps 34 of a diaper 3A shown in FIG. 8C.

Otherwise, the configuration is similar to that of Embodiment 1, and like elements will be denoted by like reference numerals and will not be further described below.

Production Method:
Next, a method for producing the diaper 3A will be described. Note that the following description will focus on what is different from the method for producing the diaper 3A of Embodiment 1 described above.

Figure 5:
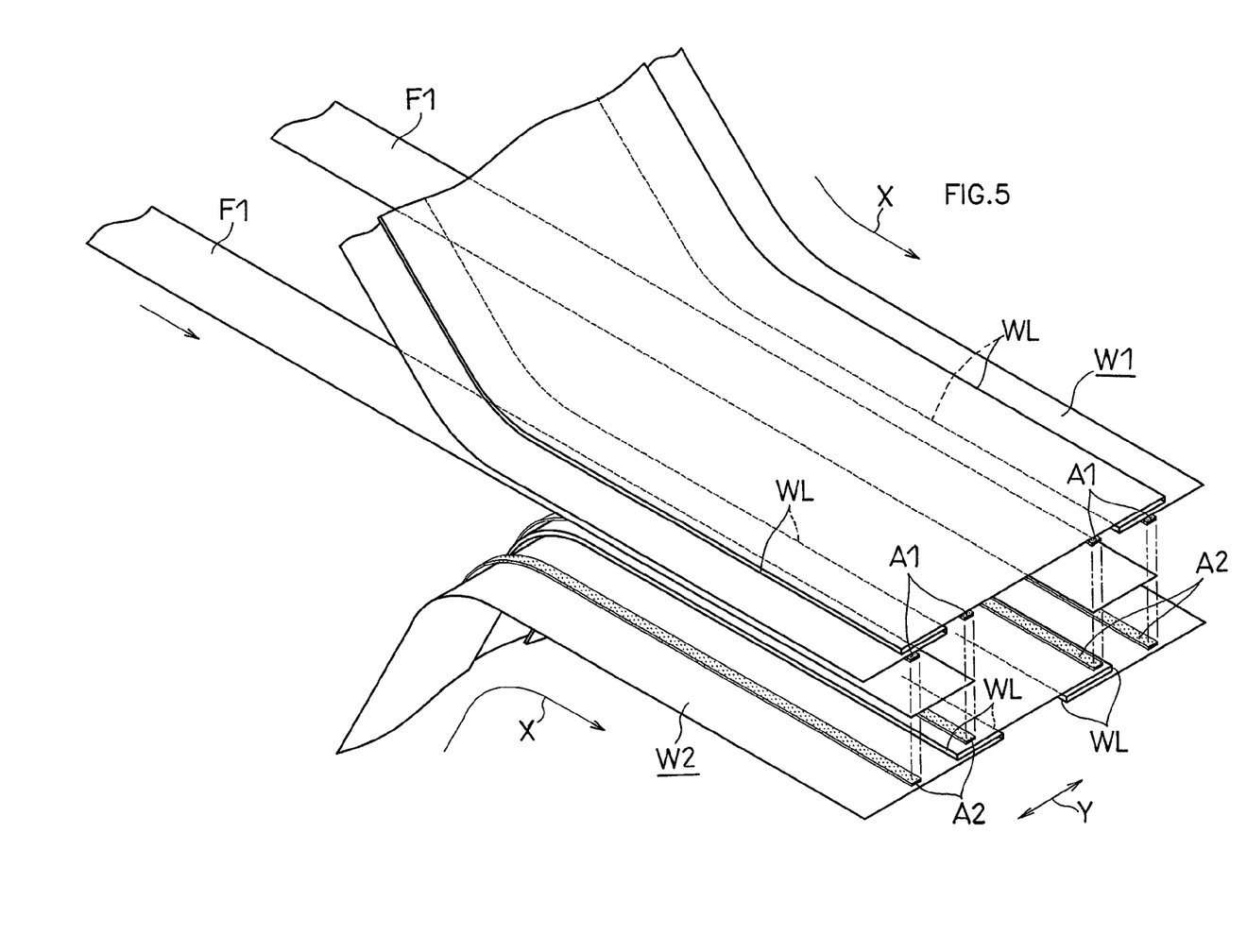
FIG. 5 is a schematic perspective view showing a part of a production step for producing a laminated stretchable sheet according to Embodiment 2 of the present invention.
Figure 6A:
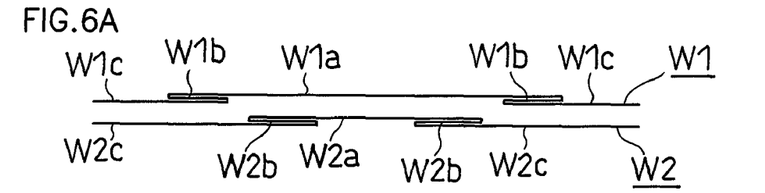
FIGS. 6A, 6B, 6C and 6D are schematic cross-sectional views showing a method for producing a laminated stretchable sheet.

First, as shown in FIG. 5, the first and second continuous sheets W1 and W2, which are non-woven fabrics, are bent and then folded up along the folding lines WL, thereby forming the slack portions W1b and W2b of FIG. 6A.

Figure 6B:
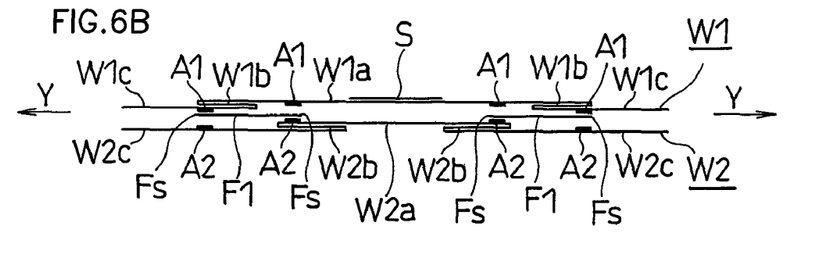

Then, as shown in FIGS. 5 and 6B, the sheet-like elastic members F1 and F1, which are stretchable in the width direction Y generally perpendicular to the carrying direction X of the continuous sheets W1 and W2, are placed between the continuous sheets W1 and W2 while being aligned with, and bridging between, the slack portions W1b and W2b, thus producing the laminated stretchable sheet W.

As shown in FIG. 5, the elastic members F1 are supplied so as to be sandwiched between the continuous sheets W1 and W2.

An adhesive is applied in advance on predetermined portions A1 and A2 of the continuous sheets W1 and W2, as shown in FIGS. 5 and 6B, and therefore only the opposite end portions Fs of the elastic member F1 in the width direction Y are attached by the adhesive. The adhesive may be, for example, a hotmelt resin, or the like.

Figure 7:
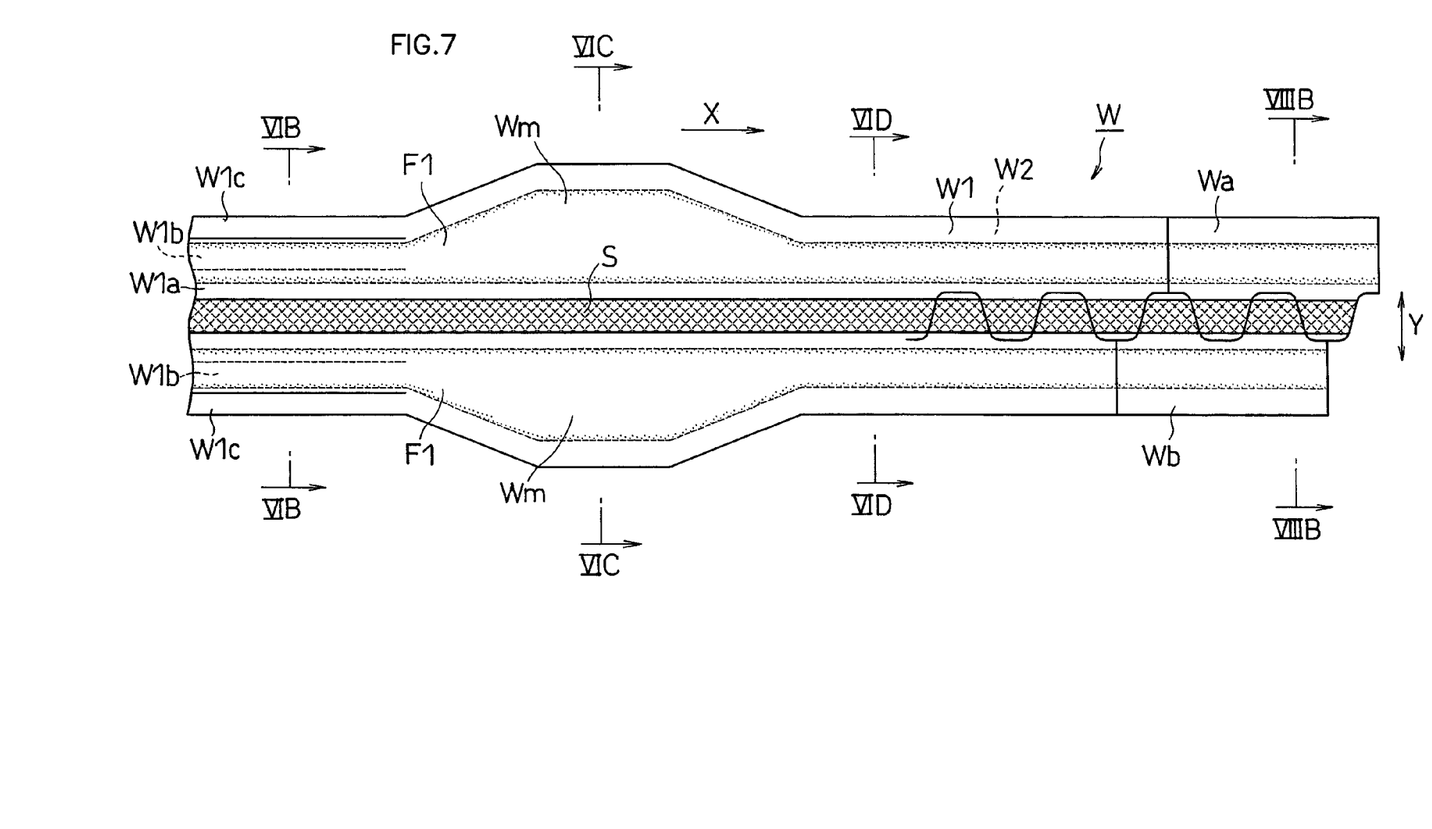
FIG. 7 is a schematic plan view showing a method for producing a laminated stretchable sheet.

Together with the placement of the elastic members F1, a touch fastener S shown in FIG. 7 is attached to the central portion W1a of one continuous sheet W1.

Figure 6C:
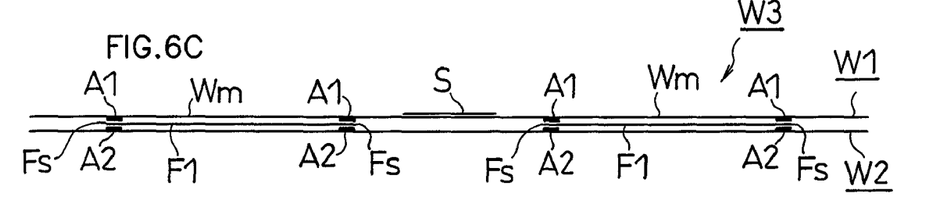

Then, as the slack portions W1b and W2b shown in FIG. 6B are drawn in the width direction Y, the slack portions W1b and W2b are drawn outwardly in the width direction Y, while the elastic members F1 are stretched, as shown in FIG. 6C, thus producing the composite sheet W3. After the stretching, the ultrasonic attachment is done in the intermediate portion Wm shown in FIG. 7, thereby welding together the continuous sheets W1 and W2 at a plurality of positions.

Note that the welding may be done so that vent holes H1 and 112 (FIG. 11B) to be described later are formed. In such a case, it is preferred that the elastic members F1 are placed between the continuous sheets W1 and W2 while being slightly stretched toward the carrying direction X (FIG. 5).

Figure 6D:
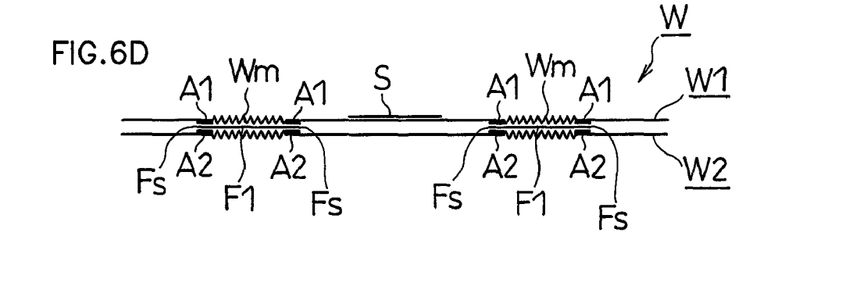

After the ultrasonic attachment, the stretching of the intermediate portion Wm and the elastic members F1 is released so that they are allowed to return to the free length, as shown in FIG. 6D, thus producing the laminated stretchable sheet W.

Figure 8A:
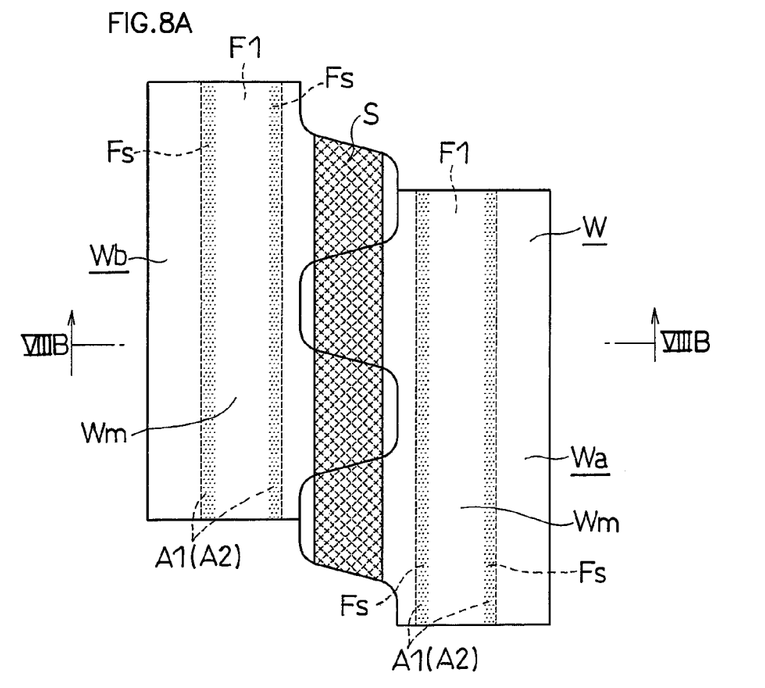
FIG. 8A is a schematic plan view showing an example of a laminated stretchable sheet.
Figure 8B:
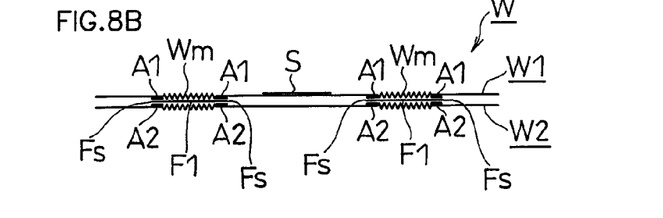
FIG. 8B is a schematic cross-sectional view thereof.
Figure 8C:
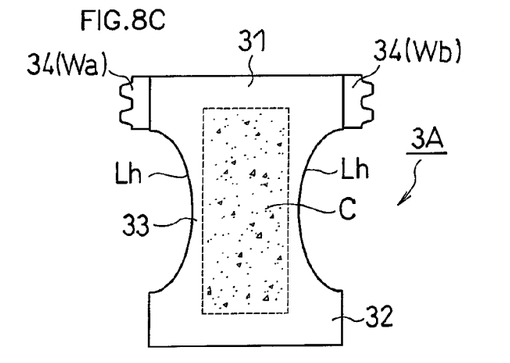
FIG. 8C is a schematic plan view showing a diaper.

Then, as shown in FIG. 8A, the central portion of the laminated stretchable sheet W is slit in a predetermined wave-shaped pattern along the carrying direction X, and the laminated stretchable sheet W is cut off along the width direction Y into pieces of a predetermined length, thus producing the cut-off sheets Wa and Wb to be the flaps 34.

It is preferred that after the slitting, the phases of the continuous cut-off sheets are aligned with each other by, for example, relatively lowering the carrying speed of one continuous cut-off sheet from that of the other continuous cut-off sheet. After the cutting off, the phases of the two cut-off sheets Wa and Wb may be aligned with each other by, for example, relatively lowering the carrying speed of one cut-off sheet Wa (Wb). Then, the cut-off sheets Wa and Wb may be attached to the opposite end portions of the rear torso portion 31 of the diaper 3A, thus forming the diaper 3A.

Figure 9:
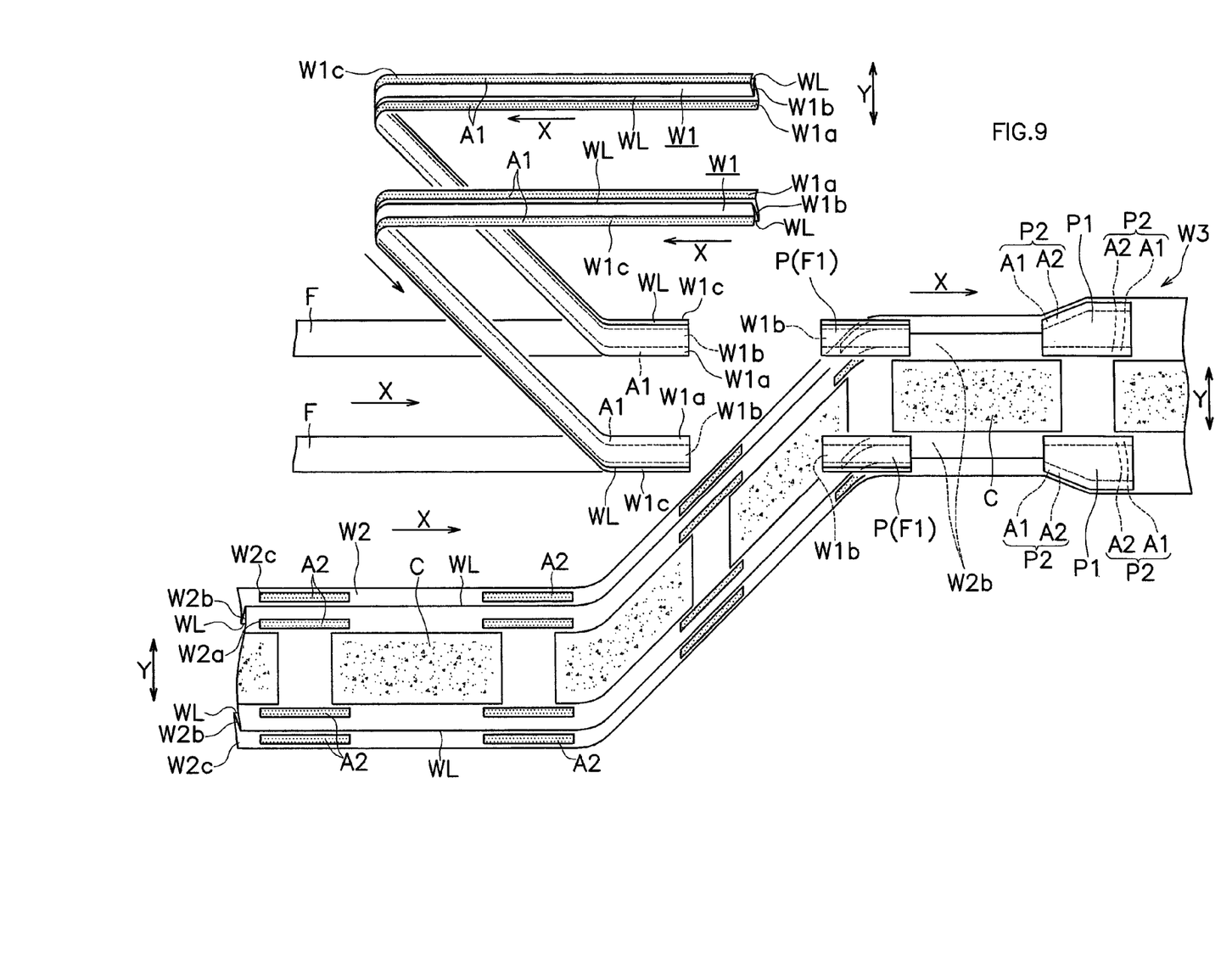
FIG. 9 is a schematic perspective view showing a production step for producing a laminated stretchable sheet according to a variation of the present invention.
Figure 10:
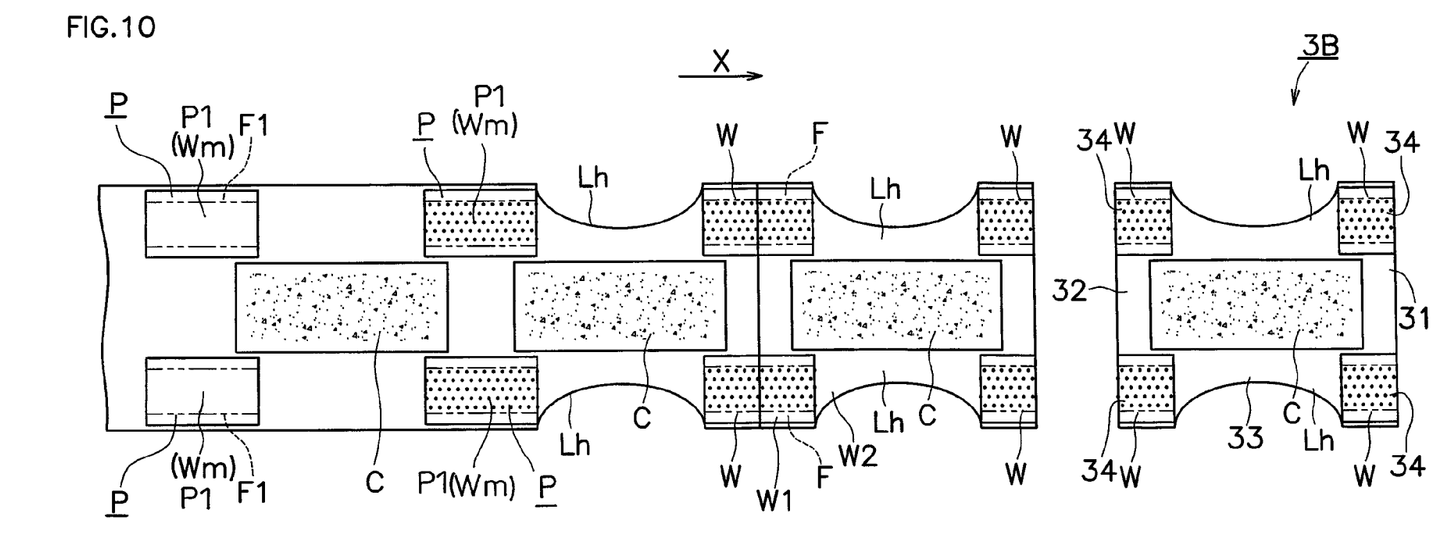
FIG. 10 is a schematic plan view showing a production step for producing a worn article.

FIGS. 9 and 10 Show a Variation.

Diaper 3b:

As shown in FIG. 10, the laminated stretchable sheet W is formed in each of the flap 34 portions of the torso portions 31 and 32 of a diaper 3B. In the portion of the laminated stretchable sheet W, a sheet-like elastic sheet (elastic member) F shown in FIG. 9 is placed while being sandwiched between non-woven fabrics.

Otherwise, the configuration is similar to that of Embodiment 1, and like elements will be denoted by like reference numerals and will not be further described below.

Production Method:

Next, a method for producing the diaper 3B (FIG. 10) will be described.

As shown in FIG. 9, first, a pair of first non-woven fabrics W1 and W1 are bent along the folding lines WL into a generally Z-shaped pattern and then they are folded up, thereby forming the slack portions W1b and W1b. Next, an adhesive is applied on the first bonding portions A1 and A1 at the opposite end portions W1a and W1c of the first non-woven fabrics W1 and W1 in the width direction Y, and the first non-woven fabrics W1 and W1 are bonded to the elastic sheets F and F, respectively. Since the first bonding portion A1 is provided continuously in the carrying direction X of the first non-woven fabric W1, the elastic sheet F and the first non-woven fabric W1 are attached to each other by the adhesive in the first bonding portion A1 as the elastic sheet F is placed to be laid on the first non-woven fabric W1.

Then, the first non-woven fabric W1 and the elastic sheet F, which have been attached together, are cut off to thereby obtain a pair of cut-off panels P each including the elastic sheet piece F1.

Note that the pair of cut-off panels P may be produced by slitting a single sheet of the first non-woven fabric W1 and the elastic sheet F. That is, the pair of cut-off panels P may be produced by bending, and slackening, left and right end portions of a single continuous first non-woven fabric W1 into a generally Z-shape pattern or a generally Ω-shape pattern and then further folding them up, thereby forming a pair of slack portions W1b and W1b, and bonding the first non-woven fabric W1 to the single continuous elastic sheet F, after which the web is slit between the two slack portions W1b and W1b and cut off into pieces of a predetermined length.

On the other hand, the second non-woven fabric W2, which is a continuous web, to be the diaper main body is carried in the carrying direction X of the second non-woven fabric W2. The second non-woven fabric W2 is folded up along the folding lines WL, thereby forming a pair of slack portions W2b, and the core portions C are attached intermittently in a generally central portion in the width direction Y.

Then, the pairs of cut-off panels P are placed intermittently on opposite end portions of the second non-woven fabric W2 in the width direction Y.

Herein, an adhesive is applied in advance at predetermined regular intervals on second bonding portions A2 near the opposite end portions of the second non-woven fabric W2 in the width direction Y, and during the placement, the first bonding portions A1, which are the opposite end portions of the elastic sheet piece F1 in the width direction Y, are attached to the second non-woven fabric W2 by the adhesive.

As the cut-off panels P are placed on the second non-woven fabric W2, the composite sheet W3 is produced, in which the elastic sheet piece F1 is sandwiched between the two non-woven fabrics W1 and W2. The elastic sheet piece F1 is in a state where the opposite end portions P2 thereof are attached to the first non-woven fabric W1 and the second non-woven fabric W2 by the first bonding portions A1 and A1 and the second bonding portions A2 and A2, respectively, and the intermediate portion P1 between the opposite end portions P2 has not yet been attached to the non-woven fabrics W1 and W2 at this point.

Then, as the composite sheet W3 is pulled in the width direction Y, the slack portions W1b and W2b are drawn outwardly in the width direction Y, and the elastic sheet piece F1 is stretched. After the stretching, the intermediate portion P1 (Wm) of the elastic sheet piece F1 shown in FIG. 10 is ultrasonically attached, wherein the cut-off panel P is welded to the first non-woven fabric W1 and the second non-woven fabric W2 at a plurality of positions, thus producing the laminated stretchable sheet W.

Note that the welding may be done so that vent holes H1 and H2 to be described later are formed. In such a case, it is preferred that the elastic sheet F is placed between the non-woven fabrics W1 and W2 while being slightly stretched toward the carrying direction X (FIG. 9).

Then, the leg holes Lh of FIG. 10 are formed, and the non-woven fabrics W1 and W2 and the elastic sheet piece F1 are cut off into individual diapers 3B so that the laminated stretchable sheet W is divided equally in the carrying direction X.

Sealing Apparatus 1:

Next, an example of a sealing apparatus used for the ultrasonic attachment will be described.

Figure 11C:
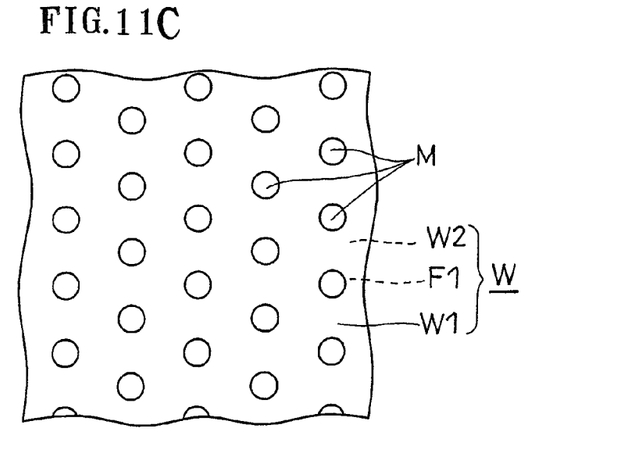
FIG. 11C is a schematic plan view showing a laminated stretchable sheet.
Figure 12:
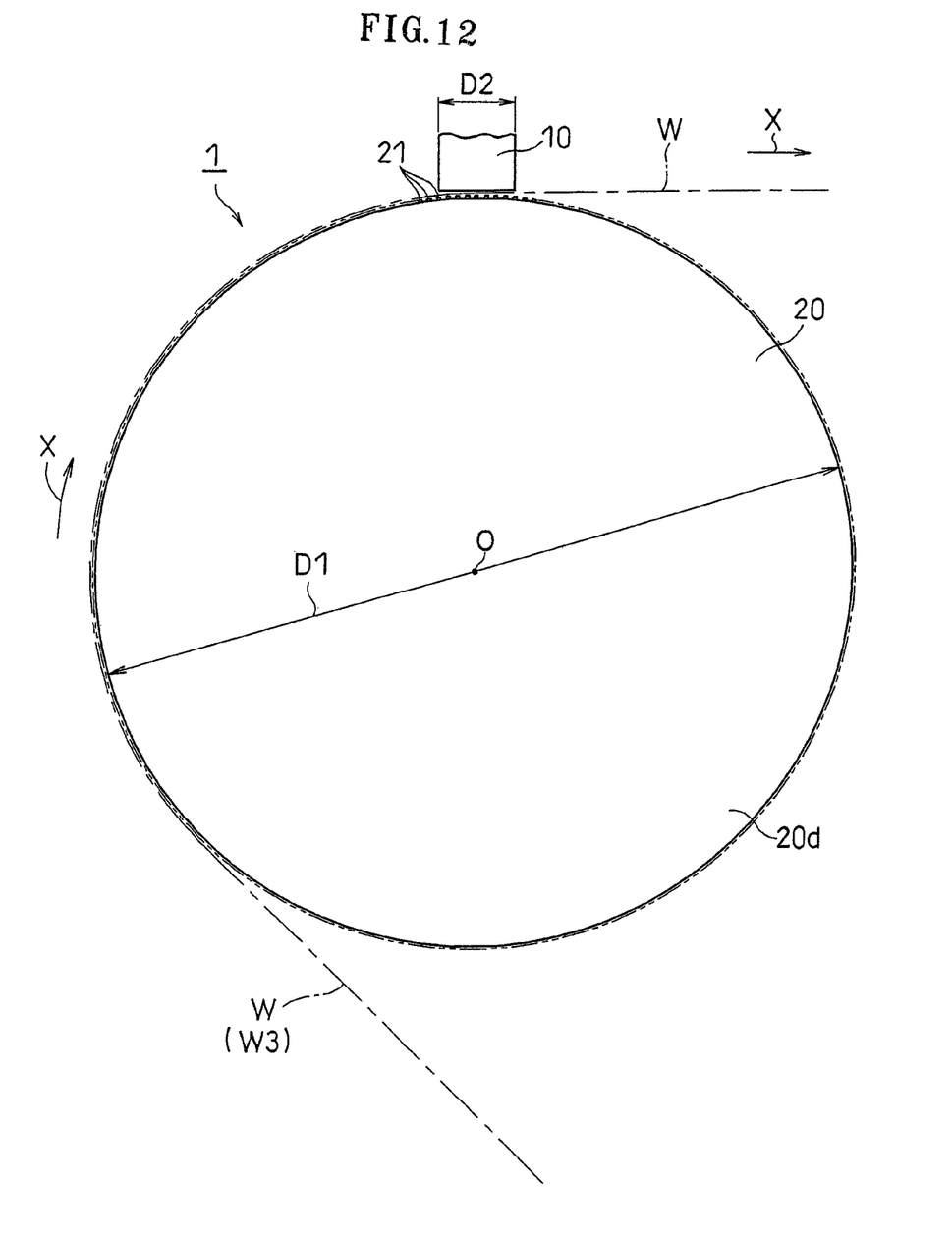
FIG. 12 is a schematic side view showing a sealing apparatus.

As shown in FIG. 12, a sealing apparatus 1 includes an anvil 20 having a large number of protrusions 21 corresponding to the attachment positions M (FIG. 11C) for carrying the composite sheet W3, and a horn 10 for applying a vibration energy on the composite sheet. W3 in cooperation with the anvil 20. The horn 10 has a flat head surface.

In the anvil 20, the protrusions 21 are formed along the periphery of a drum 20d that rotates about the axis including the point O. The composite sheet W3 is carried in the carrying direction X, entailed by the rotation of the drum 20d. The protrusions 21 are provided on the drum 20d at positions corresponding to the pattern of the attachment positions M shown in FIG. 11C.

Figure 13A:
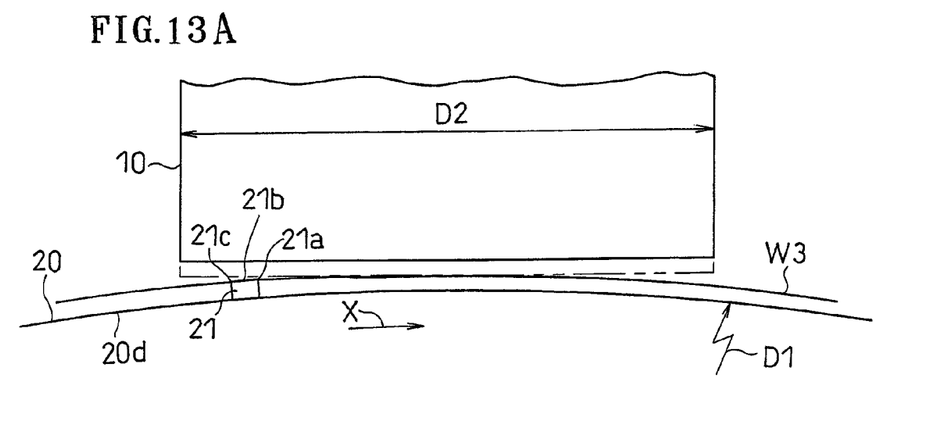
FIGS. 13A, 13B and 13C are schematic side views showing a method for producing a laminated stretchable sheet.
Figure 13B:
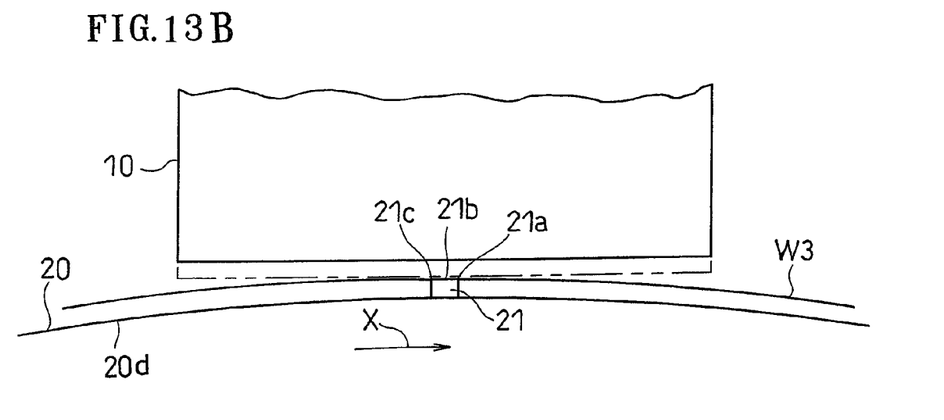
Figure 13C:
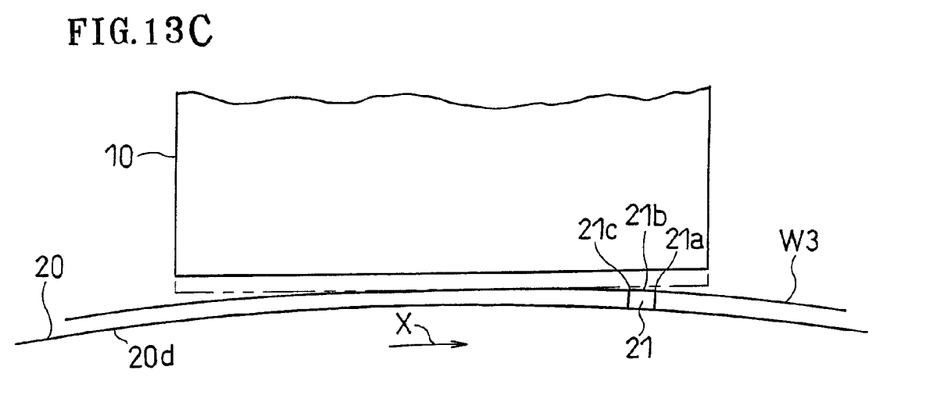

FIGS. 13A, 13B and 13C show only one of the large number of protrusions 21. The protrusion 21 is formed in a generally cylindrical shape. The protrusion 21 includes a flat portion 21b which is flat and capable of facing the horn 10, and edge portions 21a and 21c, which are portions of the peripheral edge of the flat portion 21b of the generally cylindrical shape.

Principle on which Vent Holes H1 and H2 are Formed:

Next, the principle on which the vent holes H1 and 112 are formed will be described. Note that in the following description, the composite sheet W3 is denoted simply by a single solid line, and one of the protrusions 21 is illustrated.

Figure 11A:
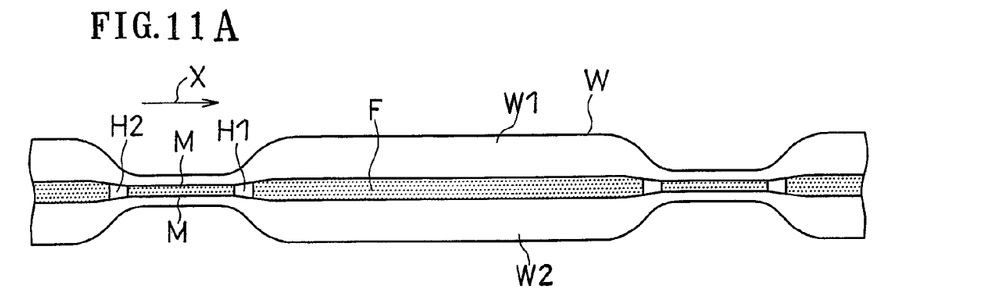
FIG. 11A is a schematic cross-sectional view showing a laminated stretchable sheet.

Referring to FIG. 13A, first, as one protrusion 21 starts facing the horn 10, only a portion of the protrusion 21 contacts the horn 10 via the composite sheet W3 because the drum 20d has a curvature. That is, as the frontward portion 21a of the peripheral edge of the edge portion of the protrusion 21 (the end portion on the downstream side in the rotation direction of the drum 20d) contacts the vibrating horn 10, the elastic sheet F shown in FIG. 11A is cut along this contact portion, thus forming a slit in the elastic sheet F. Due to the tensile force of the elastic sheet F in the flow direction, the slit widens in the carrying direction X, thus forming the first vent hole H1.

Then, as shown in FIG. 13B, as the drum 20d rotates, the flat portion 21b of the protrusions 21 contacts the vibrating horn 10, thereby ultrasonically welding the non-woven fabrics W1 and W2 and the elastic sheet F with each other.

After the welding, as shown in FIG. 13C, as the drum 20d further rotates and the rearward portion 21c of the peripheral edge of the edge portion of the protrusions 21 contacts the vibrating horn 10, the elastic sheet F shown in FIG. 11A is cut, as described above, along this contact portion, thus forming the second vent hole H2 in the elastic sheet F.

Figure 11B:
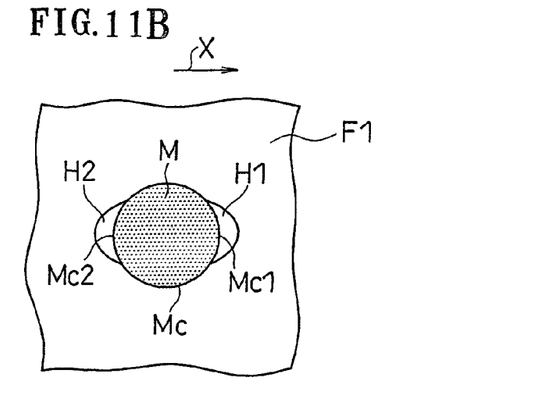
FIG. 11B is a schematic plan view showing an elastic member.

Thus, as shown in FIG. 11B, in the elastic sheet F, the attachment positions M at which the elastic sheet F is welded to the non-woven fabrics W1 and W2 are formed, and the vent holes H1 and H2 are formed by the cut portions Mc1 and Mc2, obtained by cutting only the frontward and rearward portions, in the flow direction X, of the outer edge Mc of the attachment position M. Herein, since the elastic sheet F is carried in a slightly stretched state also in the carrying direction X, as described above, the elastic sheet F is easily cut when a cutting force is applied on the elastic sheet F by the edge portions 21a and 21c of the protrusion 21. Moreover, since the elastic sheet F is cut in a slit shape by the edge portions 21a and 21c, the vent holes H1 and H2 will be slightly widened in the flow direction X, as shown in FIG. 11B.

Next, a diameter D1 of the drum 20d of FIG. 12 and a width D2 of the horn shown will be discussed.

As described above, in order for the frontward and rearward portions in the rotation direction of the protrusion 21 to serve as edges, the diameter D1 of the drum 20d needs to be small enough, and the width D2 of the horn 10 needs to be large enough.

On the other hand, the diameter D1 of the drum 20d needs to be large enough in view of the mechanical strength.

In view of the above, the diameter D1 of the drum 20d is preferably 50 mm to 400 mm, and most preferably 100 mm to 300 mm. The width D2 of the horn is preferably 10 mm to 40 mm, and most preferably 15 mm to 30 mm.

On the other hand, the elastic sheet F may be a thin film-like sheet having a thickness of 20 μm to 300 μm, preferably 30 μm to 200 μm, and most preferably 40 μm to 100 μm.

A thicker film will decrease the economical efficiency and the cutting property, and a thinner film will have a decreased mechanical strength, thus failing to obtain a predetermined stretchability.

Note that while the attachment between the continuous sheets and the elastic member is made by ultrasonic attachment in the embodiments above, an attachment method by thermal welding such as heat sealing, for example, may be used as an alternative attachment method.

INDUSTRIAL APPLICABILITY

The present invention can be applied to a laminated stretchable sheet and the production thereof.

The invention claimed is:

1. A method for producing a laminated stretchable sheet, the method comprising:
   a step of slackening a continuous sheet, which is continuous, in a width direction perpendicular to a flow direction of the continuous sheet, thereby forming an elongatable slack portion in the continuous sheet;
   a step of placing an elastic member that is stretchable in the width direction of the continuous sheet on the continuous sheet so that the elastic member bridges over the slack portion;
   a step of attaching at least opposite end portions of the elastic member in the width direction to the continuous sheet, during the placement, thereby forming a composite sheet;
   a step, of stretching the slack portion and the elastic member in the width direction; and
   a step of attaching together the continuous sheet and the elastic member intermittently in an intermediate portion between the opposite end portions, while being in the stretched state.

2. A method for producing a laminated stretchable sheet according to claim 1, wherein the attachment step of the continuous sheet and the elastic member is performed by ultrasonic attachment, in which the continuous sheet is welded by applying a vibration energy thereon.

3. A method for producing a laminated stretchable sheet, the method comprising:
   a step of slackening two continuous sheets, which are continuous, in a width direction perpendicular to a flow direction of the continuous sheets, thereby forming elongatable slack portions in the continuous sheets;
   a step of carrying the two continuous sheets with the slack portions of these continuous sheets facing each other;
   a step of placing an elastic member that is stretchable in the width direction of the continuous sheets between the two continuous sheets so as to bridge over the slack portions and so as to be sandwiched between the two continuous sheets;
   a step of attaching at least opposite end portions of the elastic member in the width direction to the continuous sheets, during the placement, thereby forming a composite sheet;
   a step of stretching the slack portions and the elastic member in the width direction; and
   a step of attaching together the two continuous sheets intermittently in an intermediate portion between the opposite end portions, while being in the stretched state.

4. A method for producing a laminated stretchable sheet according to claim 3, wherein the attachment step of the two continuous sheets is performed by ultrasonic attachment, in which the continuous sheets are welded by applying a vibration energy thereon.

* * * * *